(12) United States Patent
Chen et al.

(10) Patent No.: US 7,264,797 B2
(45) Date of Patent: Sep. 4, 2007

(54) COSMETIC COMPOSITION

(75) Inventors: Liang Bin Chen, Hoffman Estates, IL (US); David A. Brewster, Buffalo Grove, IL (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 536 days.

(21) Appl. No.: 10/748,945

(22) Filed: Dec. 29, 2003

(65) Prior Publication Data

US 2005/0142086 A1 Jun. 30, 2005

(51) Int. Cl.
*A61K 8/00* (2006.01)
*A61K 8/02* (2006.01)
*A61Q 15/00* (2006.01)

(52) U.S. Cl. .............................. 424/65; 424/66; 424/68; 424/400; 424/401

(58) Field of Classification Search ................. 424/65, 424/66, 68, 400, 401
See application file for complete search history.

(56) References Cited

U.S. PATENT DOCUMENTS 3,792,068 A 2/1974 Luedders et al. ........ 260/429.3
6,325,565 B1 * 12/2001 Girardot et al. ............ 401/266
6,416,750 B1 7/2002 Harper et al. ................. 424/65
6,547,471 B1 4/2003 Tucker et al. ............... 401/206

FOREIGN PATENT DOCUMENTS

FR 2 839 953 11/2003
GB 2 080 678 2/1982
GB 2 299 506 10/1996

OTHER PUBLICATIONS

PCT International Search Report in a PCT application PCT/EP2004/013958.
Manufacturing Chemist, vol. 65, No. 3, 1994 p. 36, "*Antiperspirants and deodorants*".
Derwent Abstract of FR 2 839 953—published Nov. 28, 2003.

* cited by examiner

*Primary Examiner*—Shelley A. Dodson
(74) *Attorney, Agent, or Firm*—Karen E. Klumas

(57) ABSTRACT

A composition comprising an antiperspirant or deodorant active and which is substantially free of alcohol and has a viscosity of less than 100 centipoise and a contact angle less than 90°. A product comprising the composition marketed in a porous dome applicator.

41 Claims, No Drawings

COSMETIC COMPOSITION

FIELD OF THE INVENTION

The present invention relates to antiperspirant and/or deodorant compositions comprising an antiperspirant and/or deodorant active. More particularly, the invention is directed to antiperspirant and/or deodorant compositions for use in liquid contact applicators. The antiperspirant and/or deodorant compositions are substantially free of alcohol. Additionally, the antiperspirant and/or deodorant compositions have a contact angle of less than about 90° and have a viscosity less than 100 centipoise.

BACKGROUND OF THE INVENTION

Antiperspirant and deodorant products come in many different forms including sticks, gels, soft solids, roll-ons and aerosols. These product forms are typically packaged in different types of dispensers that are suitable for delivering the specific product form. Dispensers for such product forms can be classified as either contact dispensers (sometimes called applicators) or non-contact dispensers. Non-contact dispensers include aerosol and spray dispensers. Within the class of contact dispensers, a further differentiation can be made between a first subclass adapted to dispense flowable materials and a second subclass of dispensers which include an internal means to transport a non-flowable material, such as a solid or hard gel towards a dispensing aperture. For identification purposes, this second subclass of contact dispensers are referred to herein as "stick dispensers".

As previously stated, in stick dispensers, internal means typically transport the solid product towards a dispensing aperture. In stick dispensers, in order to apply product the solid product is contacted against the surface upon which the product is to be applied (e.g. user's underarm area). Therefore, in stick dispensers the application surface is the product itself.

Unlike stick dispensers, in the first subclass of contact dispensers referenced above the application surface is a part of the dispenser as opposed to the product itself. Such contact applicators commonly have a surface that contains on it a thin layer of the product. The product is a flowable product that will spread on the application surface of the dispenser and on the surface upon which the product is to be applied (e.g. user's underarm area). Typical examples of such applicators are roll-on or porous applicators. In such applicators a part of the dispenser acts as the application surface as opposed to the product itself. The application surface is contacted against the surface upon which the product is to be applied (e.g. user's underarm area) and a thin coating of product is transferred from the application surface to the surface upon which the product is to be applied. While roll-on type dispensers are the primary and most popular of this subclass of contact dispensers, other types of dispensers that fall within this first subclass of applicators are known, such as an applicator having an application surface which is a porous dome as disclosed in EP Application No. 03250205.6, the disclosure of which is incorporated by reference. For identification purposes, this first class of contact dispensers are referred to herein as "liquid contact applicators". For identification purposes, liquid contact applicators having a porous dome application surface, such as those disclosed in EP Application No. 03250205.6, are referred to herein as "porous dome applicators".

Compositions that have been typically used in liquid contact applicators and porous dome applicators have been subject to several problems. These compositions have typically been alcohol based in order to improve flow properties. However, the alcohol has proven to be irritating to the user's skin. Additionally, these compositions have been known to leak from known liquid contact applicators, especially porous dome applicators.

An object of the present invention is to provide compositions for use in liquid contact applicators, especially porous dome applicators. The compositions of the present invention have good flow characteristics in such applicators and are not irritating to the user.

Other objects of the present invention will become apparent to those skilled in the art by reference to the specification.

SUMMARY OF THE INVENTION

In a first aspect, the present invention is directed to an antiperspirant and/or deodorant composition comprising an antiperspirant or deodorant active and which is substantially free of alcohol, wherein the composition has a viscosity of less than 100 centipoise and a contact angle less than about 90°.

In a second aspect, the present invention is directed to an antiperspirant and/or deodorant composition comprising an antiperspirant or deodorant active, wherein the composition has a viscosity of less than 100 centipoise and a contact angle from about 20° to about 90°.

In a third aspect, the present invention is directed to a cosmetic product comprising a dispensing container and a skin treatment product wherein the dispensing container is a porous dome applicator and wherein the skin treatment product is substantially free of alcohol, has a viscosity of less than 100 centipoise and a contact angle less than about 90°.

In a fourth aspect, the present invention is directed to a cosmetic product comprising a dispensing container and a skin treatment product wherein the dispensing container is a porous dome applicator and wherein the skin treatment product has a viscosity of less than 100 centipoise and a contact angle from about 20° to about 90°.

All percentages in this specification and claims, unless indicated otherwise, are intended to be percentages by weight.

All numerical ranges in this specification and claims are intended to be modified by the term about.

As used herein, the term "comprising" means that a specified material or element is present, optionally together a further material or element, and includes including, made up of, composed of, consisting and/or consisting essentially of.

For a more complete understanding of the above and other features and advantages of the invention, reference should be made to the following detailed description of preferred embodiments.

DETAILED DESCRIPTION OF THE INVENTION

As mentioned hereinabove, in accordance with the various aspects, the invention is directed to a composition comprising an antiperspirant or deodorant active and which is substantially free of alcohol, wherein the composition has a viscosity of less than 100 centipoise (cps) and a contact angle less than 90°. Of course, other materials may also be present depending on the nature of the material.

The present invention is directed at compositions that are not alcohol based and accordingly are substantially free of alcohol. Substantially free of alcohol as used herein means comprising less than 40% of alcohol based on total weight of the composition. In a preferred embodiment, the composition of this invention comprises less than about 30% by weight alcohol, more preferably less than about 20% by weight alcohol, more preferably less than about 10% by weight alcohol, and most preferably, less than about 2% by weight alcohol or being completely free of alcohol.

The composition preferably contains a cosmetic active such an antiperspirant or deodorant active. Cosmetic actives, are preferably incorporated in an amount of from 0.5-60%, particularly from 5 to 30% or 40% and especially from 5 or 10% to 30 or 35% of the weight of the composition and including all ranges subsumed therein.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates and activated aluminium chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which is incorporated herein by reference.

Zirconium actives can usually be represented by the empirical general formula: $ZrO(OH)_{2n-nz}B_z \cdot wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have co-ordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al), the disclosure of which is incorporated by reference. Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilized include astringent titanium salts, for example those described in GB 2299506A, the disclosure of which is incorporated by reference.

If the composition is in the form of an emulsion the antiperspirant active can be dissolved in either the disperse phase or the internal phase. In this case, the antiperspirant active will often provide from 3 to 60% by weight of the water phase (internal or disperse), particularly from 10% or 20% up to 55% or 60% of that phase. Most preferably the active will be 40%-50% by weight of the water phase.

Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™ (triclosan), Tricloban™, and Chlorhexidine warrant specific mention. A yet another class comprises biguanide salts such as are available under the trade mark Cosmosil™. A yet another class comprises chelators such as DTPA.

The chemical name of DTPA is diethylenetriaminepentaacetic acid (INCI name pentetic acid) whose structure is as follows:

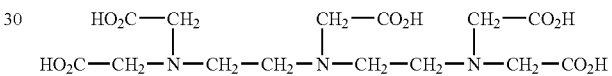

DTPA is an aminocarboxylate chelator of first transition series metals. The parent acid's CAS number is 67-43-6 and the EINECS number is 200-652-8. The pentasodium salt (Na5DTPA, INCI name pentasodium pentetate) has the CAS number 140-01-2 and an EINECs reference of 205-391-3.

Deodorant actives should be employed at an effective amount. Deodorant actives are commonly employed at a concentration of up to 1% by weight of the composition and preferably up to 0.3% by weight of the composition.

In another preferred embodiment, the composition will comprise the antiperspirant and/or deodorant active, water, and a surfactant. The water level is preferably from about 0 or 1% to about 95% based on total weight of the composition. In a preferred embodiment, the composition of this invention comprises about 40% to about 85% water by weight of the composition, more preferably about 55% to about 80% water by weight of the composition, and most preferably about 60% to about 75% water by weight of the composition and including all ranges subsumed therein. This is based on an active level of about 25%. Lower levels of active will likely correspond to higher levels of water.

The surfactant level is preferably from about 0 or 0.01% to about 10% based on total weight of the composition. In a preferred embodiment, the composition of this invention comprises about 0.5% to about 7% by weight of the composition, more preferably about 1% to about 5% by weight of the composition, and including all ranges subsumed therein.

Surfactants are included to solubilize the fragrance and other oil soluble components that may be present. It also serves to lower the contact angle of the product in order to yield optimum flow characteristics. Suitable surfactants include nonionic surfactants and especially nonionic surfactants which contain a polyalkylene oxide moiety, the residue of a fatty acid or fatty alcohol and optionally the residue of an aliphatic polyhydric alcohol linking group. Although, the surfactants may comprise a single fatty residue, they preferably contain two residues. Preferably, the surfactant is an ester surfactant, and especially a diester surfactant. The polyalkylene oxide is often polyethylene oxide, or polypropylene oxide or mixed polyethylene oxide/propylene oxide, the polymer containing from 3 to 50 and especially from 5 to 20 alkylene oxide units. The fatty acid or alcohol often contains from 12 to 24 carbons, and in many instances is linear, examples including 16, 18 or 22 linear carbons. Preferred surfactants include ceteareth-2 to 18, ceteth-2 to 16, Meroxapol 312, C11-15 Pareth 20, Isoceteth-30, Laureth 16, nonoxynol 9, oleth-20, PEG-60 castor oil, PEG 200 castor oil, PEG-20 dilaurate, PEG-20 glyceryl laurate, PEG-75 sorbitan laurate, Polysorbate 80, Poloxamer 105, Poloxamer 182, Poloxamer 407, Poloxamer 707, Poloxamer 1307, Steareth-20.

Additional surfactants include those based on silicone backbones. Examples include silicon copolyols, lauryl methicone copolyol, cetyl dimethicone copolyol, and diammonium dimethiconecopolyol sulfosuccinate, and surface functional elastomers such as DC 9011.

Especially preferred surfactants are isoceteth-20 and PEG-40 hydrogenated castor oil.

Another optional ingredient of the composition is a whitening reduction agent that decreases whitening as the product dries on the skin. Whitening reducing agents include masking oils such as aliphatic hydrocarbons, esters, siloxane fluids and polymers such as carbowaxes, as well as glycols such as propylene glycol and hexylene glycol.

Other optional ingredients of the compositions are skin benefit agents. Skin benefit agents are products which will be deposited onto the skin when the deodorant or antiperspirant composition is applied to the skin and which will impart to or maintain desirable properties for the skin. Benefit agents include components which moisturize, condition or protect the skin. Suitable benefit agents include moisturizing components, such as, for example, emollient/oils. By emollient oil is meant a substance that softens the skin and keeps it soft by retarding the decrease of its water content and/or protects the skin. A significant proportion of skin benefit agents also are capable of providing other functions to the composition. Thus, many comprise oils which can act as carriers. Others are waxes and fatty acids or alcohols which can provide structure to an oil phase, either alone or in conjunction with other materials. It will be recognized from their description which other function they provide or contribute to. It is particularly preferred in some embodiments of the invention that the deodorant or antiperspirant compositions comprise skin benefit agents such as, for example, moisturizing components. Preferred skin benefit agents include glycerin, sunflower seed oil, cocoa butter, dimethicone, and shark liver oil.

The antiperspirant composition may include other conventional ingredients. These include, for example, fragrances, emollients, bactericides, paraffinic hydrocarbons such as mineral oil and hydrogenated polyisobutene, fatty acid esters such as C12-C15 alcohols benzoate and myristyl octanoate, fatty acid esters such as isopropyl palmitate, myristyl myristate and octyl isononanoate, dicarboxylic acid esters such as diisopropyl sebacate, fatty amides such as Stearamide MEA and Lauramide DEA, polyethylene glycols and polypropylene glycols such as PEG-40 and PPG-20, polyethylene and/or polypropylene glycol ethers of C4-20 alcohols such as PPG-10 butanediol, PPG-5-Buteth-7, PPG-14 butyl ether, PPG-3-Myreth-3, and Steareth-20, and polyethylene and/or polypropylene glycol esters of C4-20 acids such as PEG-8 Distearate and PEG-10 Dioleate.

The foregoing list of materials is by way of example only and is not intended to be a comprehensive list of all potential materials that may be useful in a composition according to the invention. Obviously, the skilled worker may select those materials which provide the desired application and aesthetic characteristics of the particular form of antiperspirant composition to be produced.

An optional class of ingredients comprises moisturizing agents such as humectants. These include propylene glycol, sorbitol and especially glycerol. Moisturizing agents preferably comprise from about 0 or 1% to 20% based on total weight of the composition. In a preferred embodiment, the composition of this invention comprises about 1% to about 10% by weight of the composition, and more preferably from about 1% to about 5% by weight of the composition, and including all ranges subsumed therein. If employed, it is desirable that the amount is chosen such that the agent is retained within the carrier fluid.

Other optional ingredient can include:

skin feel improvers, such silica, or glyceryl fatty esters, e.g. glyceryl stearate, incorporated, for example, in an amount of up to about 10% based on total weight of the composition;

in addition to those previously mentioned, skin benefit agents such as allantoin or lipids, for example in an amount of up to 5% based on total weight of the composition; and Silicone based ingredients such as silicone elastomers and insoluble, non-volatile silicone, which may be one or more polyalky siloxanes, one or more polyalkylaryl siloxanes, or mixtures thereof. The silicone is insoluble in the aqueous matrix of the composition and so is present in a water based emulsified form, with the silicone present as a dispersed particles.

Suitable polyalkyl siloxanes include polydimethyl siloxanes which have the CTFA designation dimethicone. Also suitable is polydimethyl siloxane terminated with hydroxyl groups which have the CTFA designation dimethiconol. Also suitable is polydiethyl siloxane.

The polyalkylaryl siloxanes which may be used in the compositions of the invention include polymethylphenyl polysiloxane. Also suitable are silicone gums such as polydiorganosiloxanes. Specific examples include polydimethyl siloxane polymer, polydimethyl siloxane/methylvinylsiloxane copolymer, polydimethyl siloxane/methylvinylsiloxane copolymer and mixtures thereof.

Aminofunctional silicones which have the CTFA designation amodimethicone are also suitable for use in the compositions of the invention.

Compositions of the invention can further comprise other cosmetic ingredients such as colorants, preservatives, and thickeners.

As previously stated, the compositions of the present invention are defined in part by their contact angle. The contact angle is defined as the angle measured in the liquid that is formed at the junction of three phases, for example, at the solid-liquid-gas junction.

The contact angle of the compositions of the present invention were measured by image analysis on the shape of a drop of liquid resting on a horizontal solid surface (a sessile drop). The drop shape analysis method captures video images of liquid droplets and analyzes their shape and size to determine various surface properties.

The contact angles for the solutions of the present invention were measured using a FTA 4100 video drop shape analysis system. The solid substrate used in this study is an ultra high molecular weight polyethylene film with 0.020 inch thick (McMaster Part Number 85655K157). The film was first washed with a 2.5% sodium lauryl sulfate solution and rinsed with deionized water. The film was then let dry for a minimum of an hour before it was ready for use. A drop of solution (about 8 micro-liter) was dispensed using a disposable syringe with dispensing needle (a Kahnetics stainless steel dispensing needle gauge 20 with ID 0.635 mm, OD 0.914 mm, hub color yellow). The digital image was taken 15 seconds after the drop was dispensed on the solid surface.

The sessile drop was then fitted with a non-sphere fitting routine as known in the art which fits polynomials to each side of the sessile drop profile. This yields two separate contact angles, one for each side. The contact angles reported in this study are an average of these two angles.

Contact angle as used herein means the contact angle of the composition as measured by the above procedure.

Viscosity is measured in the conventional manner using a rotary viscometer (Bohlin CVOR with a C25 bob and cup geometry at 10 s$^{-1}$ at 25° C.).

The composition of the present invention will preferably have a viscosity less than 100 centipoise. In a preferred embodiment, the composition of this invention will have a viscosity less than 30 centipoise, more preferably less than 20 centipoise, even more preferably less than 15 centipoise, yet more preferably less than 10 centipoise, and most preferably less than 5 centipoise.

The compositions of the present invention may be produced by conventional processes for making liquid cosmetic compositions. The examples of the present invention were made by first blending the fragrance (and any other oil soluble materials) and the solubilizer. Then water was slowly added such that the batch will go through a phase inversion. These ingredients were mixed for an additional 5 minutes. The active solution was then added and mixed in.

The examples which follow are provided to facilitate an understanding of the present invention. The examples are not intended to limit the scope of the claims.

EXAMPLES 1-3

TABLE 1

|  | Example 1 | Example 2 | Example 3 |
| --- | --- | --- | --- |
| Arlasolv 200* | 2.0 | — | — |
| Fragrance | 1.0 | 1.0 | 1.0 |
| Water | 39.5 | 36.0 | 33.0 |
| ZAG Solution | 57.5 | 57.5 | 57.5 |
| Cremophor RH40 | — | 1.5 | 1.0 |
| Carbowax 8000 | — | 2.0 | 2.0 |
| Glycerox 767** | — | 2.0 | 5.0 |

*Isoceteth-20
**PEG-6 Capric/Caprylic Glycerides

EXAMPLES 4-11

TABLE 2

|  | Ex. 4 | Ex. 5 | Ex. 6 | Ex. 7 | Ex. 8 | Ex. 9 | Ex. 10 | Ex. 11 |
| --- | --- | --- | --- | --- | --- | --- | --- | --- |
| Water | 36.0 | 38.0 | 40.0 | 38.0 | 35.5 | 39.25 | 39.0 | 38.0 |
| ZAG Solution* | 57.5 | 57.5 | 57.5 | 57.5 | 57.5 | 57.5 | 57.5 | 57.5 |

TABLE 2-continued

|  | Ex. 4 | Ex. 5 | Ex. 6 | Ex. 7 | Ex. 8 | Ex. 9 | Ex. 10 | Ex. 11 |
| --- | --- | --- | --- | --- | --- | --- | --- | --- |
| Cremophor RH40** | 1.5 | 1.5 | 1.5 | 1.5 | 3.0 | 0.75 | 1.5 | 1.5 |
| Fragrance | 1.0 | 1.0 | 1.0 | 1.0 | 2.0 | 0.5 | — | 1.0 |
| Carbowax 8000*** | 2.0 | 2.0 | — | 2.0 | 2.0 | 2.0 | 2.0 | 2.0 |

*Aluminum Zirconium Tetrachlorohydrex GLY
**PEG-40 Hydrogenated Castor Oil
***PEG = ~150

The contact angle and viscosity of Example compositions 1-11 are shown in Table 3.

TABLE 3

| Example No. | Contact Angle | Viscosity |
| --- | --- | --- |
| 1 | 33 | 6 |
| 2 | 34 | 14 |
| 3 | 30 | 17 |
| 4 | 57 | 12 |
| 5 | 56 | 9 |
| 6 | 54 | 4 |
| 7 | 57 | 7 |
| 8 | 51 | 12 |
| 9 | 59 | 8 |
| 10 | 72 | 9 |
| 11 | 52 | 11 |

The compositions of this invention are liquids. The compositions may take the form of an emulsion. The emulsion may be an oil in water or water in oil emulsion. Examples 1-11 are all oil in water emulsions.

A composition of this invention will preferably be marketed as a product in a liquid contact applicator. More preferably a composition of this invention will preferably be marketed in a porous dome applicator.

Generally, the porous dome applicator will include a porous polymeric applicator head, an absorbent material fixed in intimate contact therewith, and a reservoir for the liquid cosmetic composition from which said composition is delivered to the absorbent material.

It should be understood, of course, that the specific forms of the invention herein illustrated and described are intended to be representative only, as certain changes may be made therein without departing from the clear teachings of the disclosure. Accordingly, reference should be made to the following appended claims in determining the full scope of the invention.

What is claimed is:

1. An antiperspirant and/or deodorant composition comprising an antiperspirant or deodorant active and which is substantially free of alcohol, wherein the composition has a viscosity of less than 30 centipoise and a contact angle less than 90° and is the form of a flowable liquid.

2. An antiperspirant and/or deodorant composition according to claim 1 further comprising water and a surfactant.

3. An antiperspirant and/or deodorant composition according to claim 1, wherein the composition comprises from about 10-50% by weight active.

4. An antiperspirant and/or deodorant composition according to claim 1, wherein the composition comprises up to about 10% by weight surfactant.

5. An antiperspirant and/or deodorant composition according to claim 1, wherein the composition comprises up to about 95% by weight water.

6. An antiperspirant and/or deodorant composition according to claim 1, wherein the composition comprises from about 55% to about 80% by weight water.

7. An antiperspirant and/or deodorant composition according to claim 1, wherein the composition comprises less than about 30% by weight alcohol.

8. An antiperspirant and/or deodorant composition according to claim 1, wherein the composition comprises less than about 20% by weight alcohol.

9. An antiperspirant and/or deodorant composition according to claim 1, wherein the composition comprises less than about 10% by weight alcohol.

10. An antiperspirant and/or deodorant composition according to claim 1, wherein the composition comprises less than about 2% by weight alcohol.

11. An antiperspirant and/or deodorant composition according to claim 1, wherein the composition has a viscosity less than 10 centipoise.

12. An antiperspirant and/or deodorant composition comprising an antiperspirant or deodorant active, wherein the composition has a viscosity of less than 100 centipoise and a contact angle from about 20° to about 90°.

13. An antiperspirant and/or deodorant composition according to claim 12 further comprising water and a surfactant.

14. An antiperspirant and/or deodorant composition according to claim 12, wherein the composition comprises from about 10-50% by weight active.

15. An antiperspirant and/or deodorant composition according to claim 12, wherein the composition comprises up to about 10% by weight surfactant.

16. An antiperspirant and/or deodorant composition according to claim 12, wherein the composition comprises up to about 95% by weight water.

17. An antiperspirant and/or deodorant composition according to claim 12, wherein the composition comprises from about 55% to about 80% by weight water.

18. An antiperspirant and/or deodorant composition according to claim 12, wherein the composition comprises less than about 30% by weight alcohol.

19. An antiperspirant and/or deodorant composition according to claim 12, wherein the composition comprises less than about 20% by weight alcohol.

20. An antiperspirant and/or deodorant composition according to claim 12, wherein the composition comprises less than about 10% by weight alcohol.

21. An antiperspirant and/or deodorant composition according to claim 12, wherein the composition comprises less than about 2% by weight alcohol.

22. An antiperspirant and/or deodorant composition according to claim 12, wherein the composition has a viscosity less than 30 centipoise.

23. An antiperspirant and/or deodorant composition according to claim 12, wherein the composition has a viscosity less than 10 centipoise.

24. A cosmetic product comprising a dispensing container and a skin treatment product which is an antiperspirant or deodorant composition comprising an antiperspirant or deodorant active, wherein the dispensing container is a porous dome applicator and wherein the skin treatment product is substantially free of alcohol, has a viscosity of less than 30 centipoise and a contact angle less than 90° and wherein the skin treatment composition is in the form of a flowable liquid.

25. A cosmetic product according to claim 24, wherein the skin treatment product comprises from about 10-50% by weight active.

26. A cosmetic product according to claim 24, wherein the skin treatment product comprises up to about 95% by weight water.

27. A cosmetic product according to claim 24, wherein the skin treatment product comprises from about 55% to about 80% by weight water.

28. A cosmetic product according to claim 24, wherein the skin treatment product comprises less than about 20% by weight alcohol.

29. A cosmetic product according to claim 24, wherein the skin treatment product comprises less than about 2% by weight alcohol.

30. A cosmetic product according to claim 24, wherein the skin treatment product has a viscosity less than 10 centipoise.

31. A cosmetic product comprising a dispensing container and a skin treatment product, wherein the dispensing container is a porous dome applicator and wherein the skin treatment product has a viscosity of less than 100 centipoise and a contact angle from about 20° to about 90°.

32. A cosmetic product according to claim 31, wherein the skin treatment product is an antiperspirant and/or deodorant composition comprising an antiperspirant or deodorant active.

33. A cosmetic product according to claim 32, wherein the skin treatment product comprises from about 10-50% by weight active.

34. A cosmetic product according to claim 31, wherein the skin treatment product comprises up to about 95% by weight water.

35. A cosmetic product according to claim 31, wherein the skin treatment product comprises from about 55% to about 80% by weight water.

36. A cosmetic product according to claim 31, wherein the skin treatment product comprises less than about 20% by weight alcohol.

37. A cosmetic product according to claim 31, wherein the skin treatment product comprises less than about 2% by weight alcohol.

38. A cosmetic product according to claim 31, wherein the skin treatment product has a viscosity less than 30 centipoise.

39. A cosmetic product according to claim 31, wherein the skin treatment product has a viscosity less than 10 centipoise.

40. An antiperspirant and/or deodorant composition according to claim 1, wherein the composition comprises a water in oil emulsion.

41. An antiperspirant and/or deodorant composition according to claim 1, wherein the composition comprises an oil in water emulsion.

* * * * *